United States Patent
Gaylord (10) Patent No.: US 9,808,369 B1
(45) Date of Patent: Nov. 7, 2017

(54) ADJUSTABLE ORTHOPEDIC BACK SUPPORT

(71) Applicant: Medical Specialties Incorporated, Charlotte, NC (US)

(72) Inventor: Eric Lee Gaylord, Weddington, NC (US)

(73) Assignee: Medical Specialties, Incorporated, Wadesboro, NC (US)

( * ) Notice: Subject to any disclaimer, the term of this patent is extended or adjusted under 35 U.S.C. 154(b) by 218 days.

(21) Appl. No.: 14/519,691

(22) Filed: Oct. 21, 2014

(51) Int. Cl.
*A61F 5/02* (2006.01)

(52) U.S. Cl.
CPC .............. *A61F 5/028* (2013.01); *A61F 5/02* (2013.01); *A61F 2220/0083* (2013.01)

(58) Field of Classification Search
CPC ...... A61F 5/00; A61F 5/01; A61F 5/02; A61F 5/028
USPC ............................................................ 602/19
See application file for complete search history.

(56) References Cited

U.S. PATENT DOCUMENTS

| 4,475,543 | A | | 10/1984 | Brooks et al. |
| 4,738,413 | A | * | 4/1988 | Spinosa ................. B64D 25/06 244/151 R |
| 5,188,586 | A | | 2/1993 | Castel et al. |
| 5,484,395 | A | | 1/1996 | Deroche |
| 5,690,609 | A | | 11/1997 | Heinze, III |
| 6,213,968 | B1 | | 4/2001 | Heinz et al. |
| 7,001,348 | B2 | | 2/2006 | Garth et al. |
| 7,101,348 | B2 | | 4/2006 | Garth et al. |
| 7,070,572 | B2 | | 7/2006 | Reinecke et al. |
| D636,494 | S | | 4/2011 | Garth et al. |
| 8,007,453 | B2 | * | 8/2011 | Richardson ........... A61F 5/0193 128/846 |
| 8,303,528 | B2 | | 1/2012 | Ingimundarson et al. |
| 8,308,670 | B2 | | 1/2012 | Sandifer et al. |
| 8,142,377 | B2 | | 3/2012 | Garth et al. |
| 8,172,779 | B2 | | 5/2012 | Ingimundarson et al. |
| 8,409,122 | B2 | * | 4/2013 | Cropper .................. A61F 5/024 128/876 |
| 8,435,196 | B2 | | 5/2013 | Bannister |
| 8,808,213 | B2 | * | 8/2014 | Hendricks ............... A61F 5/028 602/19 |
| 8,864,695 | B2 | | 10/2014 | Thornton |
| 8,926,537 | B2 | | 1/2015 | Ingimundarson et al. |
| 2012/0245502 | A1 | | 9/2012 | Garth et al. |
| 2013/0110020 | A1 | * | 5/2013 | Ingimundarson ..... A61F 5/0123 602/16 |

(Continued)

*Primary Examiner* — Keri J Nelson
(74) *Attorney, Agent, or Firm* — Schwartz Law Firm, P.C.

(57) ABSTRACT

An adjustable orthopedic back support includes a posterior panel assembly, a circumferential rail strap having ends attached to the posterior panel assembly, and at least one selectively positioned anterior panel assembly. The rail strap has an unattached intermediate length extending between its attached ends. The anterior panel assembly is carried on the unattached intermediate length of the rail strap, and is adapted for sliding linear adjustment along the rail strap relative to the posterior panel assembly. The anterior panel assembly overlaps a portion of the posterior panel assembly, and has a extension portion selectively linearly extending from the posterior panel assembly such that the back support is custom adjusted to circumferentially fit around a lumbar region of the wearer.

10 Claims, 7 Drawing Sheets

(56) References Cited

U.S. PATENT DOCUMENTS

2014/0276305 A1\* 9/2014 Cardinali ................. A61F 5/02
602/19

\* cited by examiner

ADJUSTABLE ORTHOPEDIC BACK SUPPORT

TECHNICAL FIELD AND BACKGROUND OF THE INVENTION

This invention relates broadly and generally to an adjustable orthopedic back support.

SUMMARY OF EXEMPLARY EMBODIMENTS

Various exemplary embodiments of the present invention are described below. Use of the term "exemplary" means illustrative or by way of example only, and any reference herein to "the invention" is not intended to restrict or limit the invention to exact features or steps of any one or more of the exemplary embodiments disclosed in the present specification. References to "exemplary embodiment," "one embodiment," "an embodiment," "various embodiments," and the like, may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

It is also noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

According to one exemplary embodiment, the present disclosure comprises an adjustable orthopedic back support including a posterior panel assembly, a circumferential rail strap having ends attached to the posterior panel assembly, and at least one selectively positioned anterior (or abdominal) panel assembly. The rail strap has an unattached intermediate length extending between its attached ends. The anterior panel assembly is carried on the unattached intermediate length of the rail strap, and is adapted for sliding linear adjustment along the rail strap relative to the posterior panel assembly. The anterior panel assembly overlaps a portion of the posterior panel assembly, and has a extension portion selectively linearly extending from the posterior panel assembly such that the back support is custom adjusted to circumferentially fit around a lumbar region of the wearer.

According to another exemplary embodiment, the posterior panel assembly comprises a substantially rigid back panel adapted to extend generally from an L-1 vertebra of the wearer to above an L-5 vertebra.

According to another exemplary embodiment, the posterior panel assembly further comprises first and second substantially flexible side panels extending from opposite sides of the back panel.

According to another exemplary embodiment, means are provided for adjustably interconnecting the first and second side panels to the back panel.

According to another exemplary embodiment, the means for adjustably interconnecting the first and second side panels to the back panel comprises a lace-cinch closure system. Alternative closure means may include, for example, nylon straps, hinged buckles (e.g., ski boot buckles with power straps), elastic webbing, releaseable fasteners (such as hook and loop), and the like. One specific example of an alterative closure means is disclosed in Applicant's prior issued U.S. Pat. No. 5,984,885. The complete disclosure of this prior patent is incorporated herein by reference.

According to another exemplary embodiment, the anterior panel assembly defines spaced apart laterally-slotted openings slidably receiving the unattached intermediate length of the rail strap therethrough. The slotted openings form an external window for exposing a portion of the rail strap at an outside major surface of the anterior panel assembly.

According to another exemplary embodiment, the rail strap comprises longitudinally-spaced sizing indicia adapted for being selectively exposed through the window defined by the anterior panel assembly.

According to another exemplary embodiment, the posterior panel assembly comprises loop fasteners formed with its outside major surface.

According to another exemplary embodiment, the anterior panel assembly comprises hook fasteners formed with its inside major surface. The hook fasteners are adapted to releasably mate with the loop fasteners of the posterior panel assembly.

In another exemplary embodiment, the present disclosure comprises an adjustable orthopedic back support including a posterior panel assembly, first and second circumferential rail straps, and first and second selectively positioned anterior (or abdominal) panel assemblies. The posterior panel assembly comprises a substantially rigid back panel, and first and second substantially flexible side panels extending from opposite sides of the back panel. The first circumferential rail strap has ends attached to the first side panel, and comprises an unattached intermediate length extending longitudinally between its attached ends. The second circumferential rail strap has ends attached to the second side panel, and comprises an unattached intermediate length extending longitudinally between its attached ends. The first and second anterior panel assemblies are carried on the unattached intermediate lengths of respective first and second rail straps, and are adapted for sliding linear adjustment along the rail straps relative to the side panels of the posterior panel assembly. The anterior panel assemblies overlap respective portions of the side panels, and have respective extension portions selectively linearly extending from the side panels such that the back support is custom adjusted to circumferentially fit around a lumbar region of the wearer.

According to another exemplary embodiment, the extension portion of the first anterior panel assembly comprises hook fasteners located on its inside major surface. The hook fasteners are adapted for releasably mating with complementary loop fasteners located on an outside major surface of the second anterior panel assembly.

According to another exemplary embodiment, the first anterior panel assembly comprises a handle adapted for being grasped by the wearer to separate the mated hook and loop fasteners of the first and second anterior panel assemblies.

According to another exemplary embodiment, the first anterior panel assembly comprises a finger pull adapted for being used by the wearer to separate the first anterior panel assembly and the first side panel of the posterior panel assembly.

BRIEF DESCRIPTION OF THE DRAWING

Exemplary embodiments of the present invention will hereinafter be described in conjunction with the following drawing figures, wherein like numerals denote like elements, and wherein.

DESCRIPTION OF EXEMPLARY EMBODIMENTS AND BEST MODE

The present invention is described more fully hereinafter with reference to the accompanying drawings, in which one or more exemplary embodiments of the invention are shown. Like numbers used herein refer to like elements throughout. This invention may, however, be embodied in many different forms and should not be construed as limited to the embodiments set forth herein; rather, these embodiments are provided so that this disclosure will be operative, enabling, and complete. Accordingly, the particular arrangements disclosed are meant to be illustrative only and not limiting as to the scope of the invention, which is to be given the full breadth of the appended claims and any and all equivalents thereof. Moreover, many embodiments, such as adaptations, variations, modifications, and equivalent arrangements, will be implicitly disclosed by the embodiments described herein and fall within the scope of the present invention.

Although specific terms are employed herein, they are used in a generic and descriptive sense only and not for purposes of limitation. Unless otherwise expressly defined herein, such terms are intended to be given their broad ordinary and customary meaning not inconsistent with that applicable in the relevant industry and without restriction to any specific embodiment hereinafter described. As used herein, the article "a" is intended to include one or more items. Where only one item is intended, the term "one", "single", or similar language is used. When used herein to join a list of items, the term "or" denotes at least one of the items, but does not exclude a plurality of items of the list.

For exemplary methods or processes of the invention, the sequence and/or arrangement of steps described herein are illustrative and not restrictive. Accordingly, it should be understood that, although steps of various processes or methods may be shown and described as being in a sequence or temporal arrangement, the steps of any such processes or methods are not limited to being carried out in any particular sequence or arrangement, absent an indication otherwise. Indeed, the steps in such processes or methods generally may be carried out in various different sequences and arrangements while still falling within the scope of the present invention.

Additionally, any references to advantages, benefits, unexpected results, or operability of the present invention are not intended as an affirmation that the invention has been previously reduced to practice or that any testing has been performed. Likewise, unless stated otherwise, use of verbs in the past tense (present perfect or preterit) is not intended to indicate or imply that the invention has been previously reduced to practice or that any testing has been performed.

Figure 1:
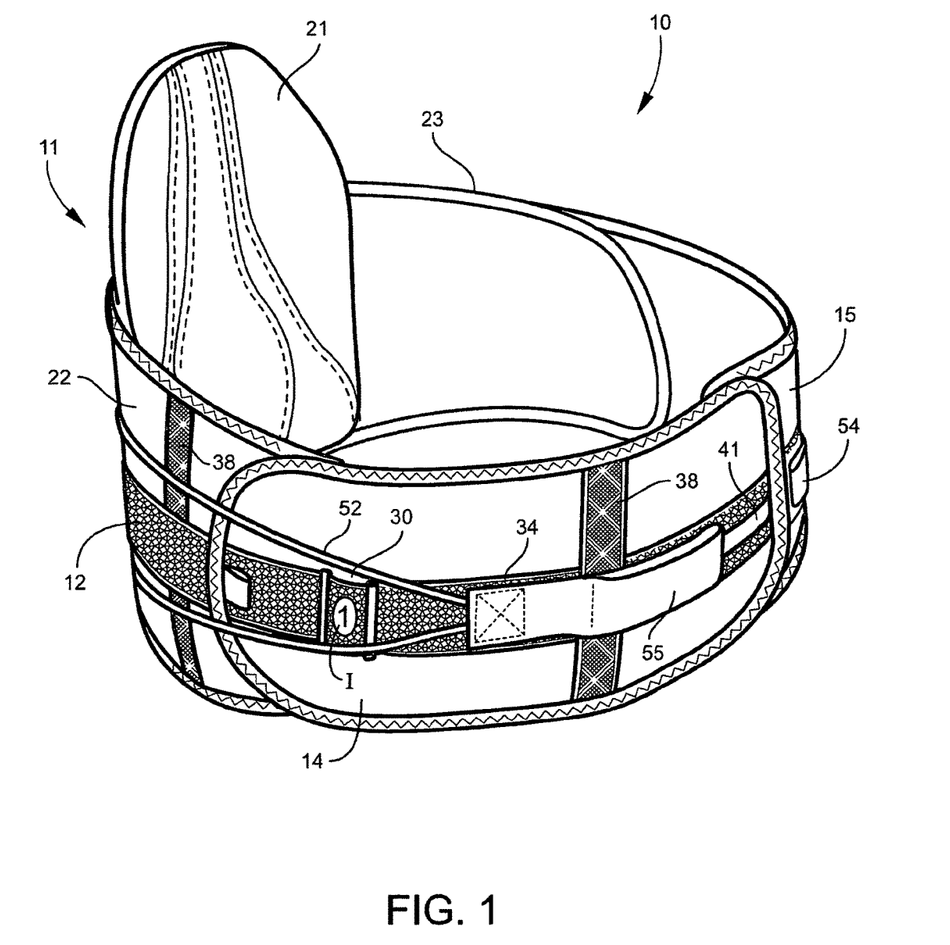
FIG. 1 is a perspective view of an adjustable orthopedic back support according to one exemplary embodiment of the present disclosure.
Figure 2:
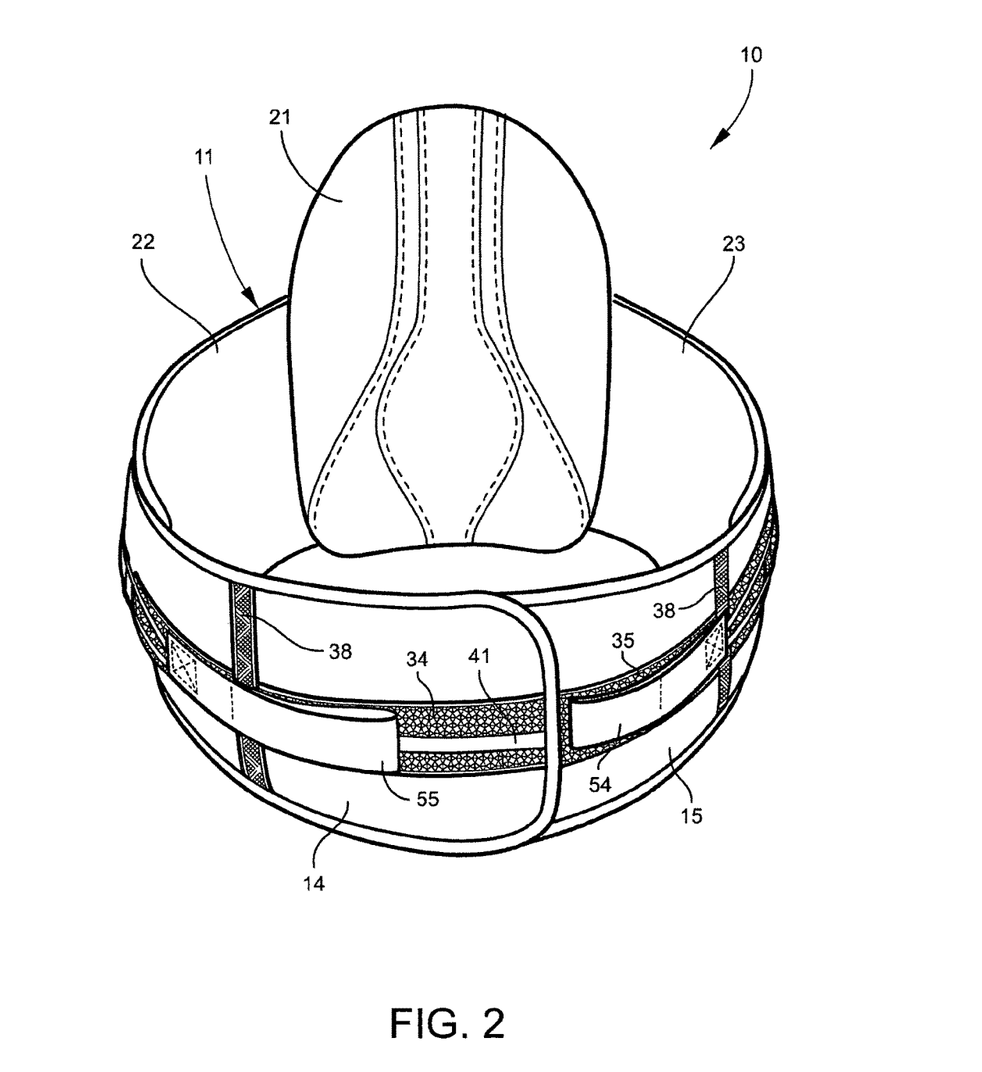
FIG. 2 is a front perspective view of the exemplary back support
Figure 3:
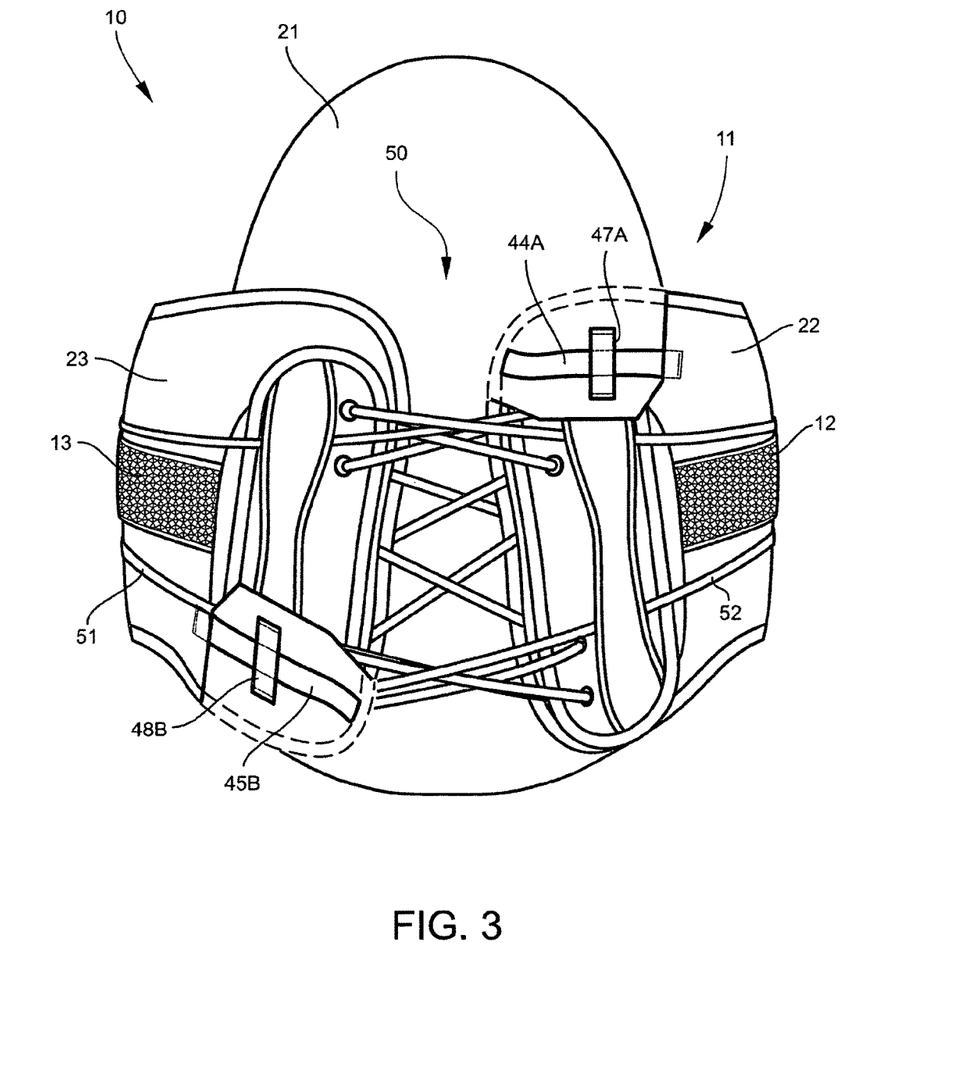
FIG. 3 is a back view of the exemplary back support, and showing portions of the side panels broken away to illustrate their adjustable positioning relative to the back panel.

Referring now specifically to the drawings, an adjustable orthopedic back support according to one exemplary embodiment of the present disclosure is illustrated in FIGS. 1-3 and shown generally at broad reference numeral 10. The exemplary back support 10 comprises a custom-fit lumbar orthosis with contoured pendulous abdomen design and sagittal control adapted to produce intracavitary pressure, thereby reducing the load on intervertebral discs and surrounding musculoskeletal structures of the lumbar spine. In various applications, the exemplary back support 10 provides lumbar stabilization and postural support, and may be used for relieving chronic and acute low back pain resulting from degenerative disc disease, lumbar muscle strains, lumbar ligamentous sprains, and other back and spine ailments.

In the exemplary embodiment shown, the present back support 10 incorporates a posterior panel assembly 11, first and second non-stretch circumferential rail straps 12, 13 attached to the posterior panel assembly 11, and first and second selectively positioned anterior panel assemblies 14, 15 adjustably carried (traveling) on the rail straps 12, 13, which are themselves attached to the posterior panel assembly 11. The exemplary posterior panel assembly 11 includes a substantially rigid back panel 21, and first and second substantially flexible (or semi-flexible) side panels 22, 23. The side panels 22, 23 extend in substantial linear alignment from opposite sides of the back panel 21 and along a longitudinal axis "X" (See FIG. 7) of the back support 10. The anterior panel assemblies 14, 15 are likewise substantially flexible or semi-flexible, and are linearly aligned along axis "X" with each other and with the side panels 22, 23 of posterior panel assembly 11. The exemplary anterior panel assemblies 14, 15 have a generally low-profile design intended to avoid interference when bending at the waist and to reduce wearer discomfort when seated. Each of the anterior panel assemblies 14, 15, back panel 21, and side panels 22, 23 has opposing inside outside major surfaces—the inside major surface adapted to reside nearest the body of the wearer, and the outside major surface residing away from the body. The anterior panel assemblies 14, 15, back panel 21, and side panels 22, 23 may be fabricated of any suitable medical grade non-stretch textile material, such as woven nylon, with durable lockstitch construction.

The exemplary back panel 21 may comprise a substantially rigid or semi-rigid contoured lumbosacral support insert positioned to reside generally between the sacrococcygeal junction and the T-9 vertebra of the wearer; and more specifically in one embodiment, from the L-1 vertebra to above the L-5 vertebra. The insert may be fabricated from any suitable thermoplastic (e.g., polyethylene) sheet material, thermoplastic foam, composite material, or the like, and can be moldable to custom fit the wearer. The exemplary panel insert is between 0.02 and 0.5 inches thick, and may be secured to the back support 21 in any conventional manner such as by sewing, gluing with textile adhesives or other bonding agents, removably or permanently positioning the insert within a pocket, or releasably fastening the insert to either side of the panel 21. In alternative embodiments, the insert may comprise a removable heatable or coolable gel type pad.

Figure 4:
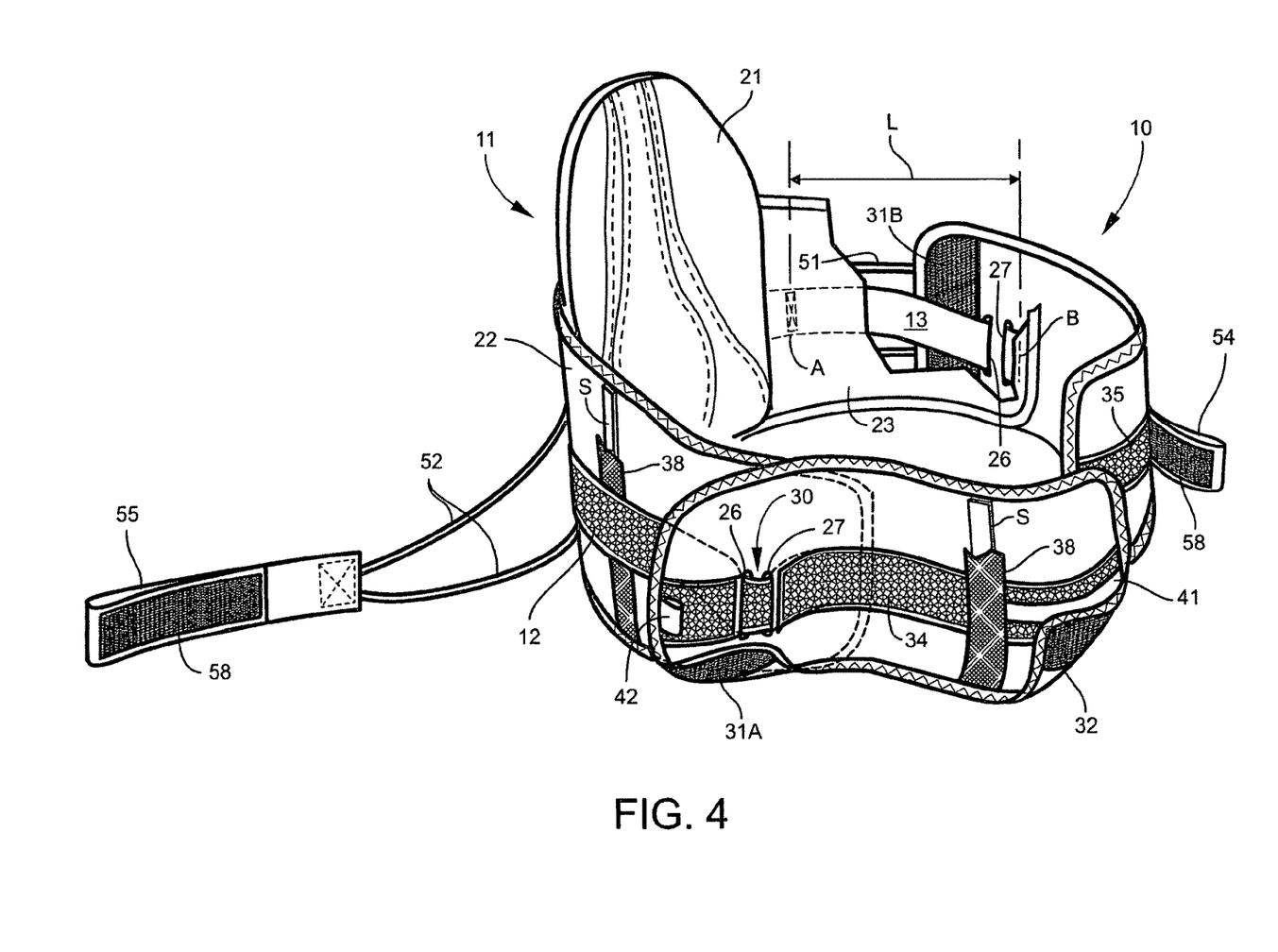
FIG. 4 is a further perspective view of the exemplary back support with portions broken away, folded, or separated to illustrate otherwise hidden components of the assembly.
Figure 5:
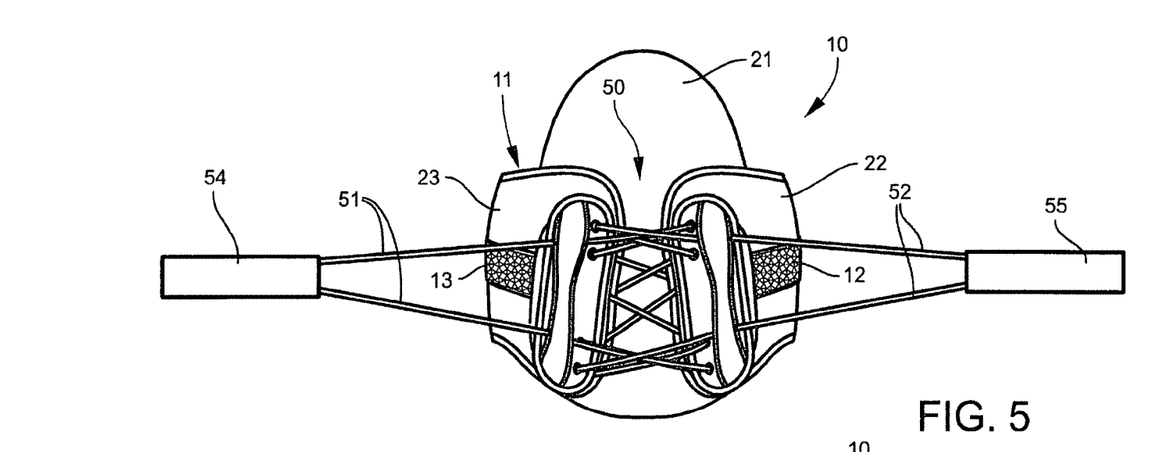
FIGS. 5 and 6 are views demonstrating operation of the lace-cinch closure assembly for closing the gap between proximal ends of the side panels, thereby tightening the circumferential fit of the back support around the waist of the wearer.
Figure 6:
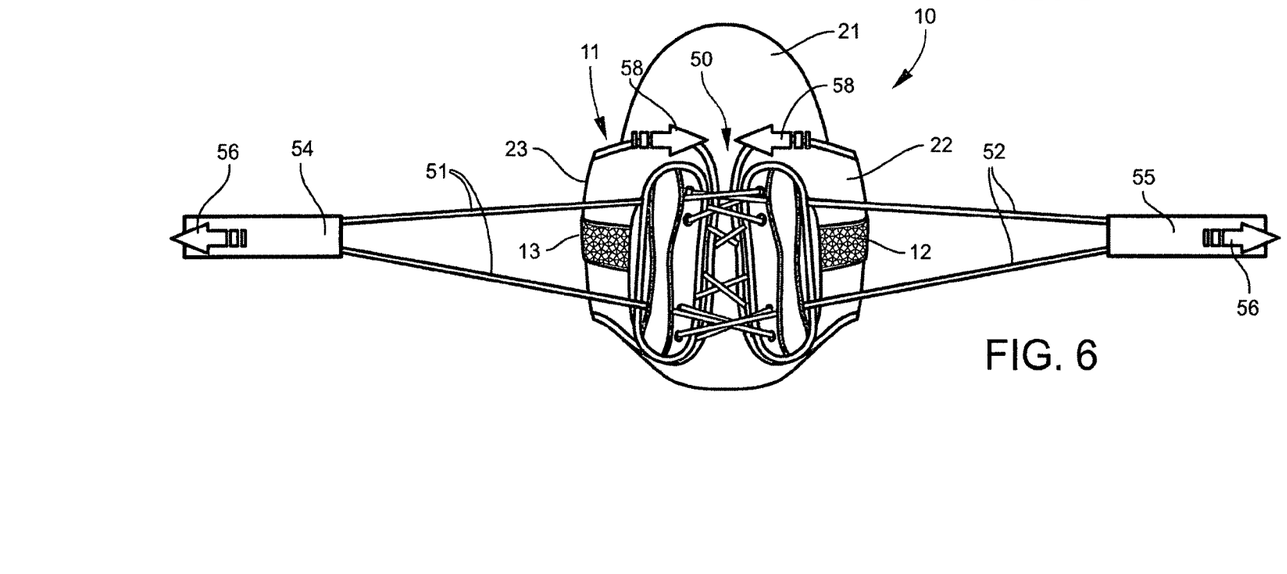

As best shown in FIG. 4, the circumferential rail straps 12, 13 of the back support 10 are attached (e.g., by sewing) at respective opposite ends "A" and "B" to side panels 22, 23 of the posterior panel assembly 11, and have respective unattached intermediate lengths "L" extending longitudinally between the attached ends "A" and "B". The rail straps 12, 13 are formed and attached in an identical manner at corresponding locations on the side panels 22, 23 and with substantially equal unattached lengths "L". The first and second anterior panel assemblies 14, 15 are secured to the rail straps 12, 13, and define respective spaced apart laterally-slotted openings 26, 27, which slidably receive the unattached intermediate lengths "L" of the rail straps 12, 13. The rail straps 12, 13 enable sliding linear adjustment of the anterior panel assemblies 14, 15 relative to the posterior panel assembly 11, and along the longitudinal axis "X" (See FIG. 7) of the back support 10 to thereby adjustably increase or reduce an overall length of the back support 10. The slotted openings 26, 27 of each anterior panel assembly 14, 15 form an external window 30 for exposing a portion of the rail strap 12, 13. As discussed further below, the anterior panel assemblies 14, 15 overlap respective portions of the side panels 22, 23, and have respective extension portions selectively linearly extending from the side panels 22, 23 along the longitudinal axis "X" such that the size of back support 10 may be custom adjusted to circumferentially fit around a lumbar region of the wearer.

The inside major surfaces of anterior panel assemblies 14, 15 comprise lateral (or vertical) hook fastener strips 31A, 31B at respective proximal ends which releasably mate with complementary loop fasteners located on the outside major surface of both side panels 22, 23. The loop fasteners may be formed inherently in the woven fabric construction of side panels 22, 23, and may be thicker and more heavily concentrated along outer surfaces of the longitudinal rail straps 12, 13. An additional lateral hook fastener strip 32 is located at the inside major surface of anterior panel assembly 14 at its distal end to releasably mate with complementary loop fasteners located on the outside major surface of panel assembly 15 at its distal end, thereby releasably and adjustable securing the back support 10 to the wearer. Both anterior panel assemblies 14, 15 may comprise longitudinal non-stretch (e.g., woven nylon) loop straps 34, 35 sewn to their respective outside major surfaces for added dimensional stability and increased holding strength when mated with the hook fasteners. The lateral hook fastener strips 31A, 31B, 32 extend only about 1-3 inches inwardly from the proximal/distal edges of panel assemblies 14, 15 to avoid contacting the wearer. No hook fasteners are located on the inside major surface of panel assembly 15 outside of the proximal fastener strip 31B. Additionally, the posterior panel assembly 11 and anterior panel assemblies 14, 15 may comprise soft plush linings (outside the area of hook fasteners) allowing the back support 10 to be worn comfortably against the skin. For added lateral stiffness, the exemplary side panels 22, 23 of the posterior panel assembly 11 and anterior panel assemblies 14, 15 may comprise respective semi-rigid thin plastic stays "S" sewn in lateral pockets 38. The stays "S" are positioned generally perpendicular to the longitudinal axis "X" of the back support 10.

As best shown in FIGS. 2, 4, 10, and 10A, the exemplary anterior panel assembly 14 comprises a fabric handle 41 adapted for being grasped by the wearer (See FIG. 10A) when applying and tightening the back support 10 circumferentially around the lumbar region to create the desired level of compression, and to separate the mated hook and loop fasteners of the anterior panel assemblies 14, 15 when removing the back support 10. The anterior panel assembly 14 may also comprise a looped finger pull 42 at its proximal edge for being used by the wearer to separate the mated fasteners of the panel assembly 14 and side panel 22 of the posterior panel assembly 11.

Referring to FIGS. 3, 4, 5 and 6, the semi-flexible side panels 22, 23 of the exemplary posterior panel assembly 11 overlap portions of the rigid back panel 21 adjacent an outside major surface of the back panel 21. As best shown in FIG. 3, the side panels 22, 23 are slidably secured to the back panel 21 by respective pairs of top and bottom laterally-spaced fabric rails 44A (identical bottom rail not shown) and 45B (identical top rail not shown) sewn to the outside of panel 21, and extending through corresponding top and bottom loops 47A (identical bottom loop not shown) and 48B (identical top loop not shown) sewn to the inside of side panels 22 and 23. The side panels 22, 23 are adjustably interconnected at respective proximal ends by a lace-cinch (or pulley-lace) closure system 50. The closure system 50 includes tensioning laces 51, 52 attached to pull straps 54, 55. When the straps 54, 55 are grasped and pulled by the wearer, as indicated by arrows 56, the side panels 22, 23 pull together to close the gap between their proximal ends, as indicated by arrows 58, thereby further tightening the back support 10 circumferentially around the wearer. After tensioning the laces 51, 52, the pull straps 54, 55 are secured using hook fasteners 58 (FIG. 4) to the non-stretch loop straps 34, 35 located on outside major surfaces of the anterior panel assemblies 14, 15. The exemplary closure system 50 provides a combined 6-to-1 mechanical advantage and an increased adjustable range of fit for any given size. The present back support 10 may be formed in a variety of sizes (e.g., small, medium, large, extra-large) to fit waistlines ranging from 27 inches to more than 59 inches, and may comprise a separate optional extension panel (not shown) enabling expansion to up to 72 inches or more.

Figure 7:
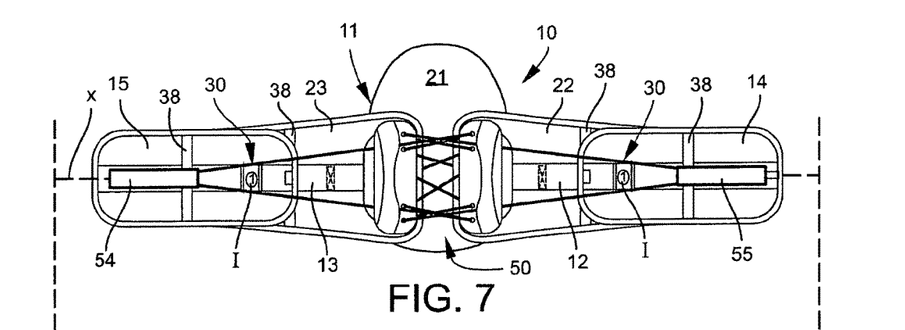
FIGS. 7, 8, and 9 illustrate respective size adjustments of the exemplary back support by repositioning the anterior panel assemblies relative to the posterior panel assembly.
Figure 8:
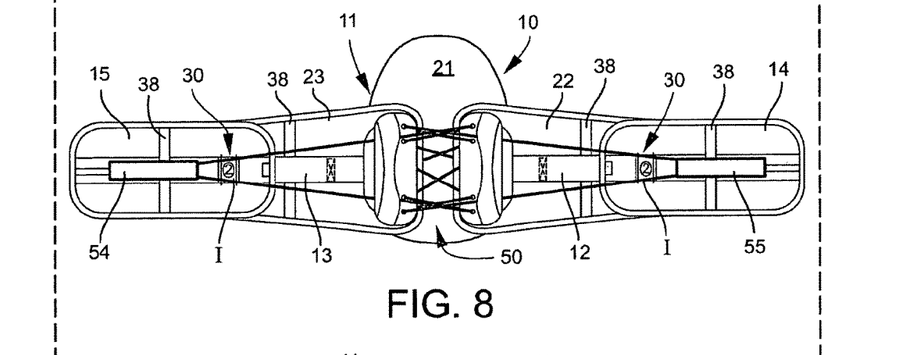
Figure 9:
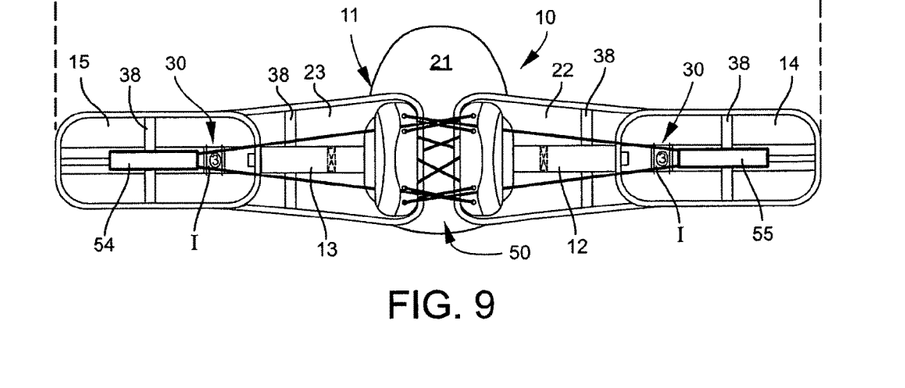
Figures 10, 10A:
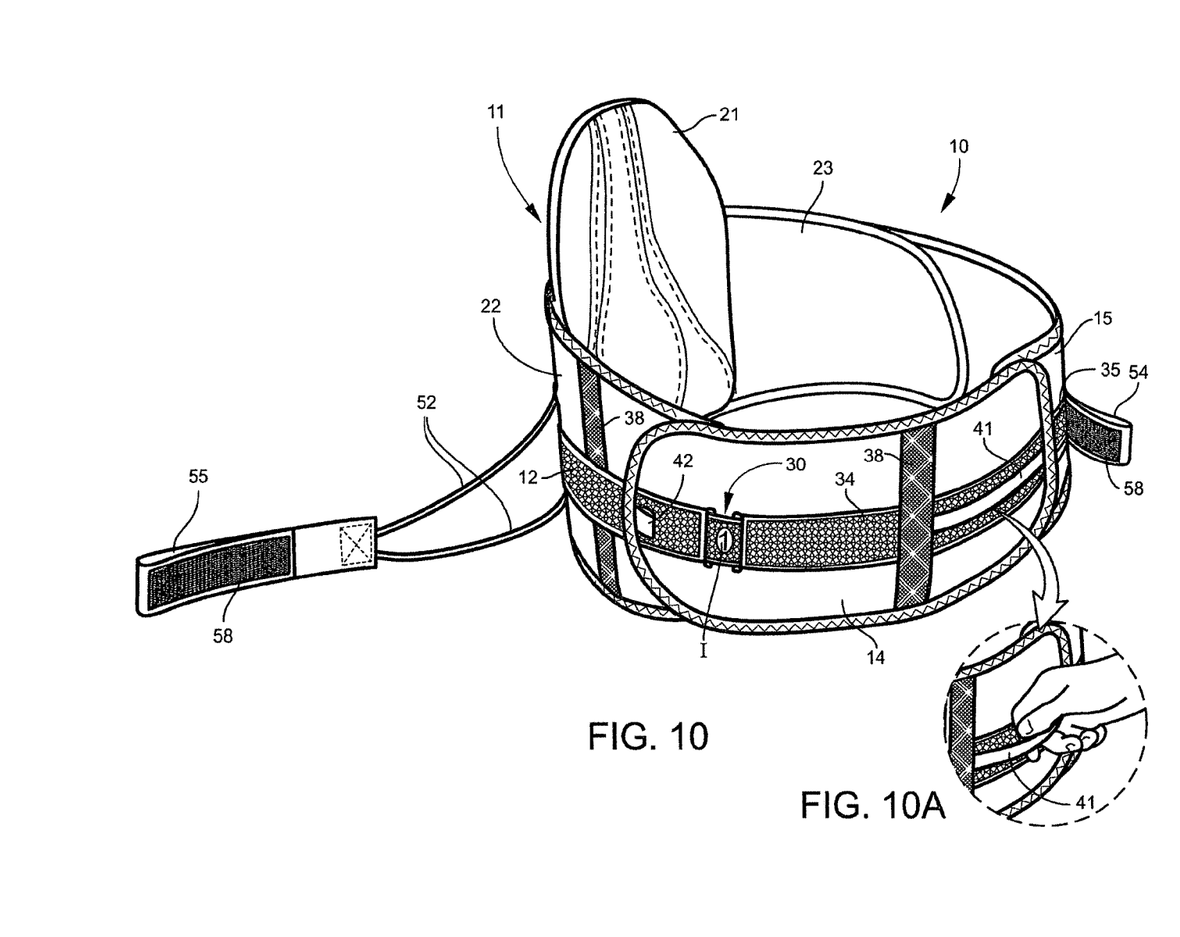
FIG. 10 is a perspective view demonstrating final assembly and size adjustment of the exemplary back support using the tensioning straps.
FIG. 10A is a view showing the panel handle grasped by the wearer.

Prior to donning or when donning, the exemplary back support 10 is custom adjusted by separating the mated fasteners securing the anterior panel assemblies 14, 15 to respective side panels 22, 23, and then linearly sliding the panel assemblies 14, 15 along the unattached lengths "L" of rail straps 12, 13 until matching sizing indicia "I" displays through the windows 30, as shown in FIGS. 7, 8, and 9. The available range of sliding adjustment corresponds to the unattached length "L" of the rail strap 12, 13 (See FIG. 4). The sizing indicia "I" is longitudinally spaced along each rail strap 12, 13, and is applied at corresponding locations on both straps 12, 13. In one embodiment, the sizing indicia "I" may comprise numbers 1, 2, 3, etc. FIGS. 7, 8, and 9 show the anterior panel assemblies 14, 15 selectively positioned at sizes 1, 2, and 3, respectively-size number 1 being the smallest shown and size number 3 being the largest shown. Alternatively, the sizing indicia "I" may comprise conventional letter indicators, such as S, M, L, and XL, or any other suitable markings. Once properly sized and applied around the waist, the wearer attaches distal ends of the anterior panel assemblies 14, 15 together at his front abdominal region. The panel assemblies 14, 15 are pulled together (e.g., using handle 41—See FIG. 10) to a desired compression, and are releasably attached by mating the inside hook fastener strip 32 of panel assembly 14 and the loops of longitudinal fastener strap 35 (and those formed with outside major surface) of panel assembly 15. As best shown in FIG. 10, after securing the back support 10 around the waist, the tensioning straps 54, 55 are grasped and pulled, as previously described, and applied to the hook fastener straps 34, 35 of anterior panel assemblies 14, 15 as a final degree of circumferential compression adjustment. The properly applied back support 10 provides substantially continuous and consistent pressure across the lumbar and abdominal regions, and thus increases the wearer's intra-abdominal pressure to reduce the load on intervertebral discs and surrounding musculoskeletal structures of the lumbar spine.

For the purposes of describing and defining the present invention it is noted that the use of relative terms, such as "substantially", "generally", "approximately", and the like, are utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

Exemplary embodiments of the present invention are described above. No element, act, or instruction used in this description should be construed as important, necessary, critical, or essential to the invention unless explicitly described as such. Although only a few of the exemplary embodiments have been described in detail herein, those skilled in the art will readily appreciate that many modifications are possible in these exemplary embodiments without materially departing from the novel teachings and advantages of this invention. Accordingly, all such modifications are intended to be included within the scope of this invention as defined in the appended claims.

In the claims, any means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. Unless the exact language "means for" (performing a particular function or step) is recited in the claims, a construction under §112, 6th paragraph is not intended. Additionally, it is not intended that the scope of patent protection afforded the present invention be defined by reading into any claim a limitation found herein that does not explicitly appear in the claim itself.

What is claimed:

1. An adjustable orthopedic back support, comprising:
    a posterior panel assembly;
    a circumferential rail strap having ends attached to said posterior panel assembly, and comprising an unattached intermediate length extending between its attached ends; and
    at least one selectively positioned anterior panel assembly carried on the unattached intermediate length of said rail strap, and adapted for sliding linear adjustment along said rail strap relative to said posterior panel assembly;
    said anterior panel assembly overlapping a portion of said posterior panel assembly, and having an extension portion selectively linearly extending from said posterior panel assembly, whereby said back support is adapted to be custom adjusted to circumferentially fit around a lumbar region of a wearer, and wherein said posterior panel assembly comprises a substantially rigid back panel adapted to extend generally from an L-1 vertebra of the wearer to above an L-5 vertebra, first and second substantially flexible side panels extending from opposite sides of said back panel, and means for adjustably interconnecting said first and second side panels together; and
    wherein said anterior panel assembly defines spaced apart laterally-slotted openings slidably receiving the unattached intermediate length of said rail strap therethrough, the slotted openings forming an external window for exposing a portion of said rail strap at an outside major surface of said anterior panel assembly, and wherein said rail strap comprises longitudinally-spaced sizing indicia adapted for being selectively exposed through the window defined by said anterior panel assembly.

2. The adjustable orthopedic back support according to claim 1, wherein said means for adjustably interconnecting the first and second side panels comprises a lace-cinch closure system.

3. The adjustable orthopedic back support according to claim 1, wherein said posterior panel assembly comprises loop fasteners formed with its outside major surface.

4. The adjustable orthopedic back support according to claim 3, wherein said anterior panel assembly comprises hook fasteners formed with its inside major surface, said hook fasteners adapted to releasably mate with the loop fasteners of said posterior panel assembly.

5. An adjustable orthopedic back support, comprising:
    a posterior panel assembly comprising a substantially rigid back panel, and first and second substantially flexible side panels extending from opposite sides of the back panel, and means for adjustably interconnecting said first and second side panels together;
    a first circumferential rail strap having ends attached to the first side panel, and comprising an unattached intermediate length extending longitudinally between its attached ends;
    a second circumferential rail strap having ends attached to the second side panel, and comprising an unattached intermediate length extending longitudinally between its attached ends;
    first and second selectively positioned anterior panel assemblies carried on the unattached intermediate lengths of respective first and second rail straps, and adapted for sliding linear adjustment along said rail straps relative to the side panels of said posterior panel assembly; and
    said anterior panel assemblies overlapping respective portions of the side panels, and having respective extension portions selectively linearly extending from the side panels, whereby said back support is adapted to be custom adjusted to circumferentially fit around a lumbar region of a wearer; and
    wherein at least one of said anterior panel assemblies defines spaced apart laterally-slotted openings slidably receiving the unattached intermediate length of one of said first and second rail straps therethrough, the slotted openings forming an external window for exposing a portion of said one of said first and second rail straps at an outside major surface of said at least one anterior panel assembly, and wherein said one of said first and second rail straps comprises longitudinally-spaced sizing indicia adapted for being selectively exposed through the window defined by said at least one anterior panel assembly.

6. The adjustable orthopedic back support according to claim 5, wherein the back panel of said posterior panel assembly is adapted to extend generally from an L-1 vertebra of the wearer to above an L-5 vertebra.

7. The adjustable orthopedic back support according to claim 5, wherein said means for adjustably interconnecting said first and second side panels comprises a lace-cinch closure system.

8. The adjustable orthopedic back support according to claim 5, wherein the extension portion of said first anterior panel assembly comprises hook fasteners located on its inside major surface, and adapted for releasably mating with complementary loop fasteners located on an outside major surface of said second anterior panel assembly.

9. The adjustable orthopedic back support according to claim 8, wherein said first anterior panel assembly comprises a handle adapted for being grasped by the wearer to separate the mated hook and loop fasteners of said first and second anterior panel assemblies.

10. The adjustable orthopedic back support according to claim 5, wherein said first anterior panel assembly comprises a finger pull adapted for being used by the wearer to separate said first anterior panel assembly and the first side panel of said posterior panel assembly.

* * * * *